(12) United States Patent
Brisebois et al.

(10) Patent No.: US 6,171,432 B1
(45) Date of Patent: Jan. 9, 2001

(54) METHOD OF MAKING A NO WASTE ABSORBENT PRODUCT

(75) Inventors: Henri Brisebois, Lachenaie (CA); Michael J. Menard, Doylestown, PA (US)

(73) Assignee: Johnson & Johnson, Inc. (CA)

( * ) Notice: Under 35 U.S.C. 154(b), the term of this patent shall be extended for 1412 days.

(21) Appl. No.: 08/511,288

(22) Filed: Aug. 4, 1995

Related U.S. Application Data

(63) Continuation of application No. 08/356,927, filed on Dec. 14, 1994, now abandoned, which is a continuation of application No. 08/169,926, filed on Dec. 17, 1993, now abandoned, which is a continuation of application No. 07/766,989, filed on Sep. 27, 1991, now abandoned.

(51) Int. Cl.[7] .............................. B32B 31/08; B32B 31/18
(52) U.S. Cl. ......................... 156/260; 156/265; 156/267; 156/270; 156/271; 156/301
(58) Field of Search .................................. 156/264, 269, 156/270, 271, 259, 260, 265, 519, 544

(56) References Cited

U.S. PATENT DOCUMENTS

| | | | |
|---|---|---|---|
| 3,744,383 | * 7/1973 | Finch et al. | 156/264 X |
| 3,878,283 | 4/1975 | Jones | 264/152 |
| 4,443,511 | * 4/1984 | Worden et al. | 264/127 X |
| 4,455,809 | * 6/1984 | Dallaserro | 53/460 X |
| 4,626,305 | * 12/1986 | Suzuki et al. | 156/265 X |
| 4,760,764 | * 8/1988 | De Jonckheere et al. | 156/259 X |

FOREIGN PATENT DOCUMENTS

| | | | |
|---|---|---|---|
| 218857 | 4/1987 | (EP) | A41B/13/02 |
| 280998 | 9/1988 | (EP) | A61F/13/18 |
| 2644694 | 9/1990 | (FR) | A61F/13/46 |
| 1217402 | 12/1967 | (GB) | A61F/13/15 |
| H1-293477 | 11/1989 | (JP) | |
| H3-185942 | 4/1991 | (JP) | |

* cited by examiner

*Primary Examiner*—Richard Crispino

(57) ABSTRACT

A novel method for manufacturing a layer of a laminated, disposable absorbent product, such as a fluid-permeable cover layer, an absorbent core layer or a fluid-impervious backing layer thereof, with a comparatively small amount of waste matter. The method comprises the steps of longitudinally cutting a continuous web of starting material according to a cyclic pattern constructed with line segments corresponding to the edge contour of the disposable absorbent product. The cutting operation divides the continuous web in two strips, each strip having a patterned longitudinal edge whose outline corresponds to the cyclic pattern. The strips are crossed and joined to one another in a parallel and in a phase relationship to form a compound web having longitudinal edges producing repeatedly the edge contour of the disposable absorbent product. The invention extends to integrating this method into an operation for manufacturing disposable absorbent products, and to a novel apparatus for carrying out the methods according to the invention and the resulting products.

23 Claims, 10 Drawing Sheets

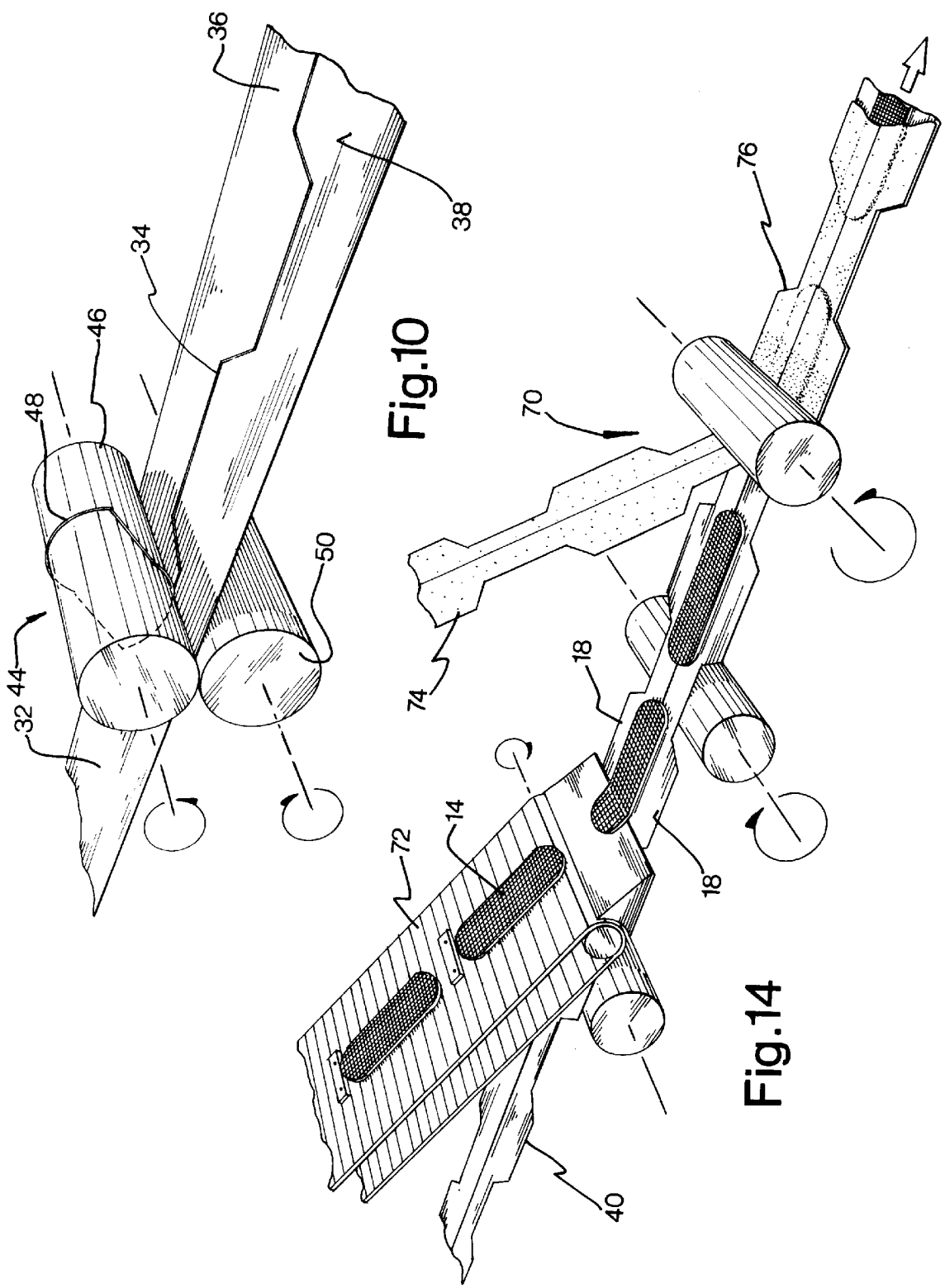

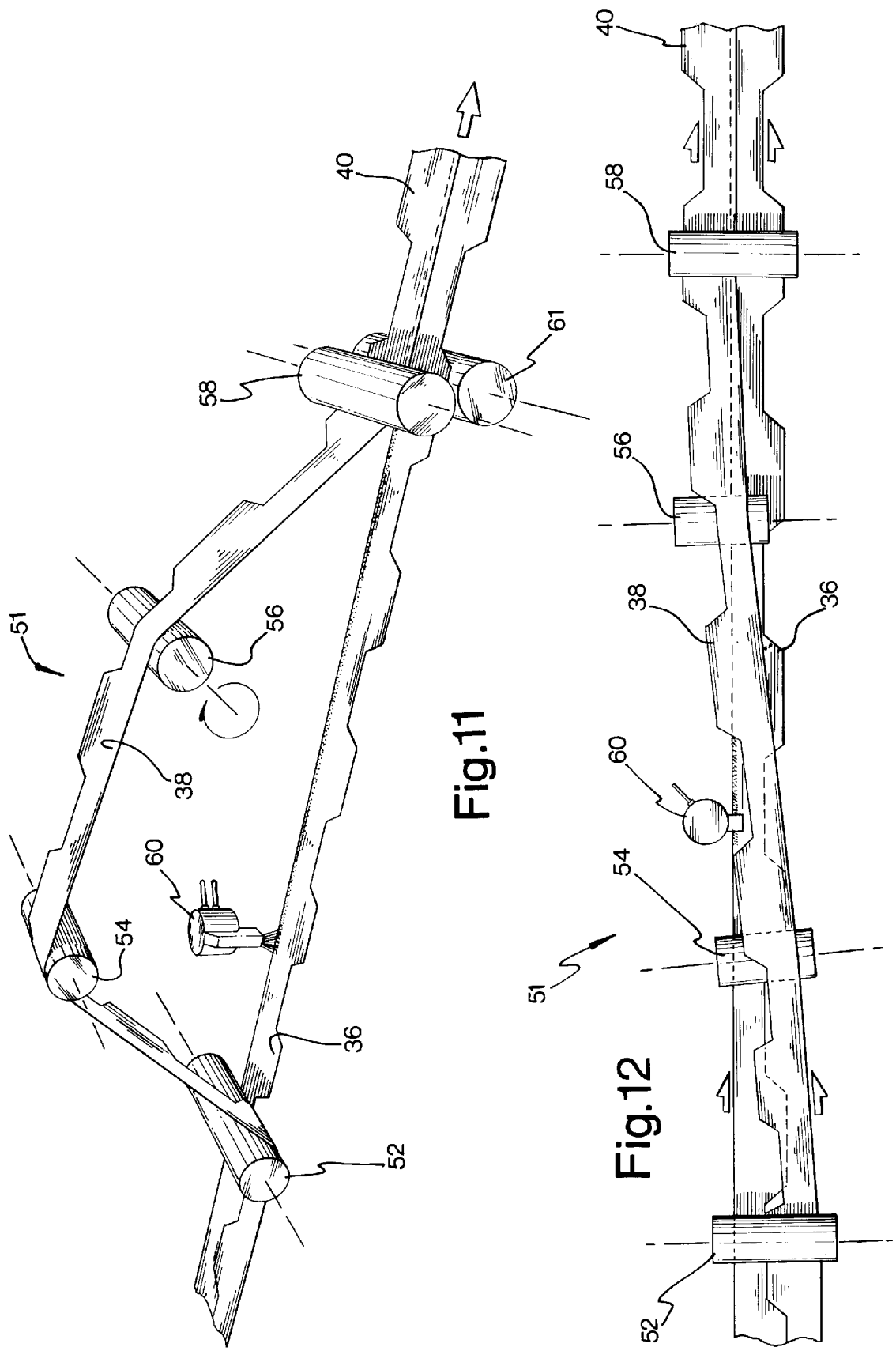

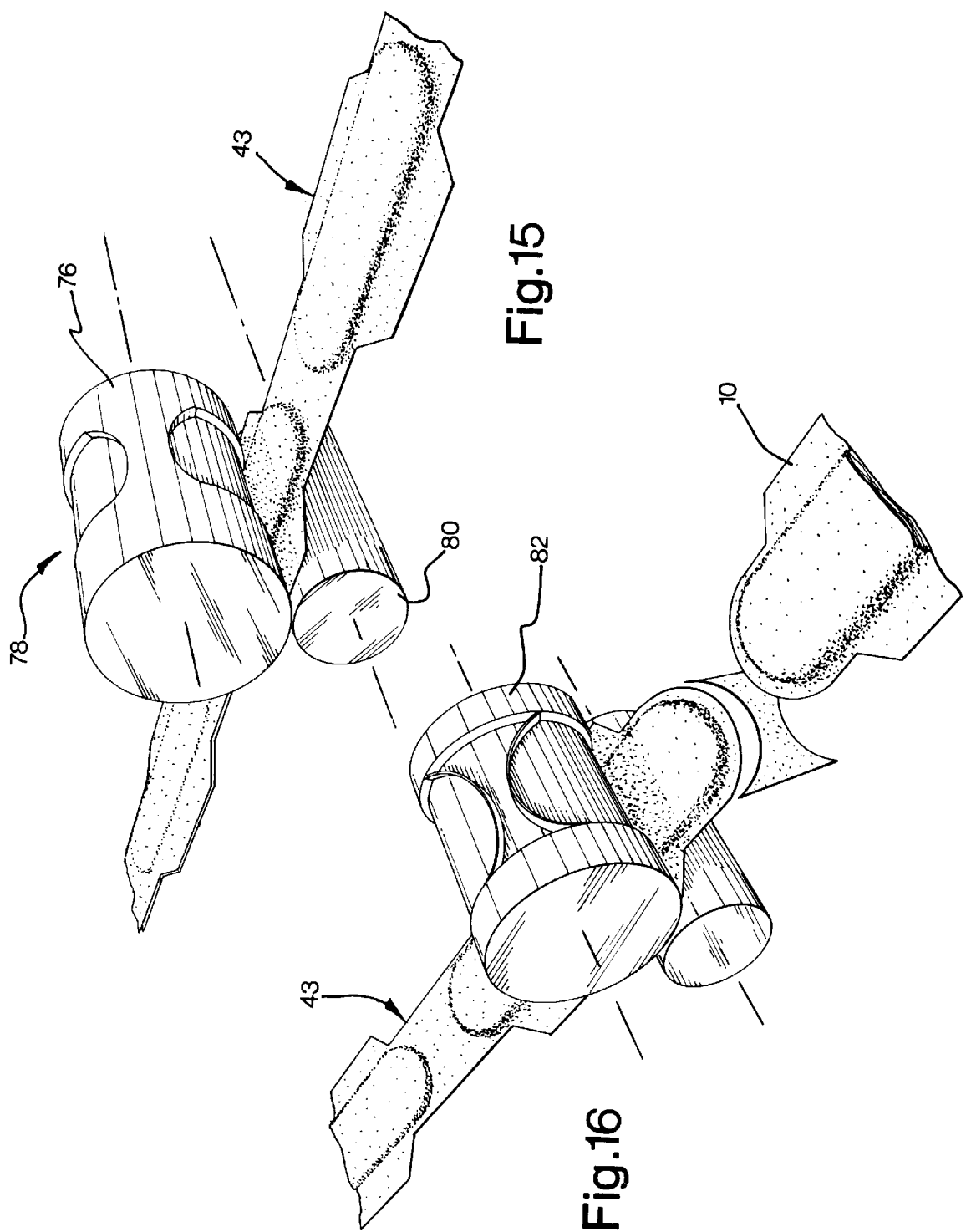

US 6,171,432 B1

METHOD OF MAKING A NO WASTE ABSORBENT PRODUCT

This is a continuation of 08/356,927 filed Dec. 14, 1994, now abandoned, which is a continuation of 08/169,926 filed Dec. 17, 1993, now abandoned, which is a continuation of 07/766,989 filed Sep. 27, 1991, now abandoned.

FIELD OF THE INVENTION

The invention relates to the art of manufacturing disposable absorbent products having a laminated construction, such as sanitary napkins, diapers, adult briefs, incontinence pads, wound dressings and the like. More specifically, the invention pertains to a method and apparatus for manufacturing with a comparatively small amount of waste matter a layer of such disposable absorbent products, such as a fluid-permeable cover layer, an absorbent core layer or the fluid-impervious backing layer, and the resulting product thereof. The invention extends to a method for manufacturing a complete disposable absorbent product and the resulting product thereof.

BACKGROUND OF THE INVENTION

A typical mass-production arrangement for manufacturing health-care, disposable, absorbent products includes an assembly line where the various components of the absorbent product are progressively combined and laminated into a continuous web which is cut transversely into discrete absorbent products.

This process is well-suited for disposable absorbent products with a periphery designed around a simple geometric figure, such as a rectangle with rounded ends. The plain side edge design of such products does not require trimming to finish the lateral edges of the absorbent products, whereby the process may be carried out without producing an inordinate amount of waste material.

To enhance the functionality of disposable absorbent products, manufacturers are now designing products with complex and sophisticated countour lines. For example, sanitary napkins have recently appeared on the market, provided with side flaps or winglets which create fastening points for the sanitary napkin on the garment facing side of the wearer's underpants. With traditional manufacturing techniques, extensive trimming is required to produce the highly irregular side edge contour of the sanitary napkin which necessarily generates a considerable amount of waste material. As a result, the manufacturing cost of the sanitary napkin increases because the starting material is used less efficiently and waste management facilities are required. Further, concurrent reduction in materials required for manufacture and reduction in waste materials requiring disposal present environmental advantages in terms of conservation of resources and reduction in waste disposal.

An object of the invention is to provide a method and an apparatus for producing a layer of a laminated, disposable absorbent product with a highly irregular contour, such as the fluid-permeable cover layer, the absorbent core layer or the fluid-impervious backing layer, with a comparatively small amount of useless by-products.

Another object of the invention is to provide a method and apparatus for manufacturing a laminated, disposable absorbent product having a highly irregular contour, with a comparatively small amount of useless by-products.

Another object of the invention is a compound layer for a laminated, disposable absorbent product, such as the fluid-permeable cover layer, the absorbent core layer or the fluid-impervious backing layer, having an arrangement of parts to permit manufacturing of the compound layer with a comparatively small amount of useless by-products.

Yet, another object of the invention is a laminated, disposable absorbent product with a structure which allows manufacture of absorbent product with a comparatively small amount of useless by-products.

SUMMARY OF THE INVENTION

The present inventors have made the unexpected discovery that a considerable reduction in useless by-products may be achieved when manufacturing laminated, disposable absorbent products with highly irregular shapes, by forming at least one layer of the disposable absorbent product from a continuous web with longitudinal edges patterned according to the absorbent product contour to substantially reduce the web trimming and cutting which would otherwise be required to give shape to the layer of the absorbent product. The patterned web is made by cutting a continuous web of starting material longitudinally into two strips, in a cyclic pattern which comprises line segments corresponding to selected sections of the edge contour of the absorbent product. The strips are then assembled in a parallel and a phase relationship to repeatedly produce the shape of the absorbent product layer.

More specifically, the invention provides a method for manufacturing a layer of a laminated, disposable absorbent product such as a fluid-permeable cover layer, an absorbent core layer or a fluid-impervious backing layer, having two opposite edges with inflected contours (for the purpose of the specification the term "inflected" should be construed to mean a deviation from a straight line forming an angularity or curvature), said method comprising the steps of:

longitudinally cutting a continuous web according to a cyclic pattern comprising a combination of line segments corresponding to a selected section of said opposite edges, thereby dividing said web in two strips, each strip having a patterned longitudinal edge whose outline corresponds to said cyclic pattern;

reassembling said strips in a parallel and selected phase relationship, with the longitudinal edges thereof which are opposite the adjacent patterned edges to produce a compound web having longitudinal edges formed by said patterned edges which are longitudinally matched to repeatedly produce the selected section; and cutting said compound web transversely at selected longitudinal positions to produce discrete layers.

Integrating this method into an operation for manufacturing disposable absorbent products involves the following steps:

prior to cutting said compound web in individual layers, absorbent core layers in a spaced apart relationship are joined with said compound web at longitudinal positions thereof selected in accordance with the positional relationship absorbent core/opposite edges of the layer of the disposable absorbent product;

retaining said absorbent core layers to said compound web; and cutting said compound web transversely between adjacent absorbent core layers to produce discrete disposable absorbent products.

In a preferred embodiment, the strips forming the compound web are united together in a partially overlapping relationship and are attached to one another adhesively or by thermal bonding. In a variant, the strips are combined in abutting relationship and individually attached to the absorbent core layer which forms a bridge holding the strips together in alignment.

Preferably, the strips forming the compound web are brought into the desired phase relationship by advancing the strips along respective paths having different lengths in order to achieve a condition of controlled longitudinal shift therebetween. In a most preferred embodiment, the strips, freshly cut, are supported on a conveyor moving in a predetermined direction. At a first position, stationary with respect to the conveyor, one of the strips is lifted off the conveyor while the other remains in supporting contact with the conveyor. At a second position, stationary with respect to the conveyor, the strip which has been previously lifted is brought back in contact with the conveyor. By this arrangement, runs of the strips between the first and second positions have different predetermined lengths to achieve the desired phase relationship between the strips.

To side match the strips, i.e. to bring the strips in a position where their longitudinal edges shaped as the cyclic pattern are brought in opposition to form the longitudinal edges of the compound web, the strips are preferably crossed one over the other. More preferably, the crossing operation is performed while the strips follow their respective paths to achieve the longitudinal shift therebetween.

The method according to the invention provides a fluid-permeable cover layer and a fluid-impervious backing layer in a laminated, disposable absorbent product, whereby a compound web of fluid-permeable material and a compound web of fluid-impervious material are assembled and subsequently sealed to one another in superposition and in alignment, around the absorbent cores. It is also possible to adopt a hybrid form of construction where the compound web providing the backing layers is made from a web of starting material having a laminated construction, comprising a bottom laminae of fluid-impervious material and a top laminae of fluid-permeable material. Host preferably, the top laminae is narrower than the bottom laminae, covering only the central area thereof. The compound web obtained from the laminated starting web has marginal portions covered with fluid-permeable material, accordingly it is no longer necessary to provide a compound web of fluid-permeable material forming the cover layer which mirrors the compound web of fluid-impervious material. It suffices to provide a plain, straight-sided web of fluid-permeable material, wide enough to encover the absorbent core, since the side edges of the fluid-impervious compound web are already furnished with fluid-permeable material.

It should be appreciated that a reversal of components is possible without departing from the spirit of the invention. The laminated compound web may comprise a bottom laminae of fluid-permeable material and a top laminae of fluid-impervious material. In this form of construction, the laminated, compound web is united with a plain, straight-sided web of fluid-impervious material to enclose the absorbent cores.

The advantage of using a hybrid compound web is twofold. Firstly, only one compound web with patterned side edges is required. Secondly, the construction of the assembly station which brings together the various components of the disposable absorbent product does not necessitate a capability to achieve registration between the webs of fluid-permeable and fluid-impervious material when joined to one another.

As embodied and broadly described herein, the invention provides a method for manufacturing laminated, disposable absorbent products, each absorbent product comprising a fluid-permeable cover layer and a fluid-impervious backing layer in a parallel and in a spaced apart relationship, and an absorbent core between said layers, one of said layers having two opposite edges with inflected contours, said absorbent core being in a predetermined positional relationship with respect to said opposite edges, said method comprising the steps of:

longitudinally cutting a continuous web according to a cyclic pattern comprising a combination of line segments corresponding to a selected section of said opposite edges, thereby dividing said web in two strips, each strip having a patterned longitudinal edge whose outline corresponds to said cyclic pattern;

reassembling said strips in a parallel and in a selected phase relationship, with the longitudinal edges thereof which are opposite the adjacent patterned edges to produce a compound web having longitudinal edges formed by said patterned edges which are longitudinally matched to repeatedly produce the selected section;

applying absorbent cores in a spaced apart relationship to said compound web at positions selected in accordance with said predetermined positional relationship;

applying an additional web to free sides of said absorbent cores, one of said compound and additional webs comprising fluid-pervious material and the other of said compound and additional webs comprising fluid-impervious material;

uniting said webs to retain said absorbent cores captive therebetween; and cutting said compound and additional webs transversely between adjacent absorbent cores to produce discrete disposable absorbent products.

As embodied and broadly described herein, the invention provides a compound layer for a laminated, disposable absorbent product, such as a fluid-permeable cover layer, an absorbent layer or a fluid-impervious backing layer, comprising:

a sheet-like body with two opposite inflected edges, said sheet-like body including two strips retained together in a generally co-planar relationship, each strip having a free edge constituting one of said opposite edges.

As embodied and broadly described herein, the invention provides a laminated, disposable absorbent product, comprising:

a backing layer of fluid-impervious material;

an absorbent layer on said backing layer; and a cover layer of fluid-permeable material in superposition to said absorbent layer, one of said layers having two opposite inflected edges, one of said layers including two strips retained together in a generally co-planar relationship, each strip having a free edge constituting one of said opposite edges.

As embodied and broadly described herein, the invention provides an apparatus for manufacturing a layer of a laminated, disposable absorbent product such as a fluid-permeable cover layer, an absorbent core layer or a fluid-impervious backing layer, said layer having two opposite edges with inflected contours, said apparatus comprising:

means for longitudinally cutting a continuous web according to a cyclic pattern comprising a combination of line segments corresponding to a selected section of said opposite edges, thereby dividing said web in two strips, each strip having a patterned longitudinal edge whose outline corresponds to said cyclic pattern;

means for reassembling said strips in a parallel and in a selected phase relationship, with the longitudinal edges thereof which are opposite said patterned edges being in adjacency, to produce a compound web having longitudinal edges formed by said patterned edges which are longitudinally matched to repeatedly produce the selected section; and means for cutting said compound web transversely at selected longitudinal positions to produce discrete layers.

As embodied and broadly described herein, the invention provides an apparatus for manufacturing laminated, disposable absorbent products, such as sanitary napkins, diapers, incontinence pads, adult briefs, wound dressings and the like, the absorbent product comprising a fluid-permeable cover layer and a fluid-impervious backing layer in a parallel and spaced apart relationship, and an absorbent core between said layers, one of said layers having two opposite edges with inflected contours, said absorbent core being in a predetermined positional relationship with respect to said opposite edges, said apparatus comprising:

means for longitudinally cutting a continuous web according to a cyclic pattern comprising a combination of line segments corresponding to a selected section of said opposite edges, thereby dividing said web in two strips, each strip having a patterned longitudinal edge whose outline corresponds to said cyclic pattern;

means for reassembling said strips in a parallel and in a selected phase relationship, with the longitudinal edges thereof which are opposite said patterned edges being in adjacency, to produce a compound web having longitudinal edges formed by said patterned edges, which are longitudinally matched to repeatedly produce said opposite edges;

means for applying absorbent cores in a spaced apart relationship to said compound web at positions selected in accordance with said predetermined positional relationship;

means for applying an additional web to free sides of said absorbent cores, one of said compound and additional webs comprising a fluid-permeable material and the other of said compound and additional webs comprising a fluid-impervious material;

means for uniting said webs to retain said absorbent cores captive therebetween; and means for cutting said compound and additional webs transversely between adjacent absorbent cores to produce discrete disposable absorbent products.

BRIEF DESCRIPTION OF THE DRAWINGS

FIG. 10 is a perspective view of a cutting station to split a continuous web according to a cyclic pattern;

FIG. 11 is a perspective view of a station to combine together the strips obtained at the cutting station of FIG. 10;

FIG. 12 is a top view of the station shown in FIG. 11;

FIG. 14 is a perspective view of an assembly station to combine together the various components of the sanitary napkin shown in FIGS. 1 and 2;

FIG. 15 is a perspective view of a station for sealing together the various layers of the continuous, laminated web assembled at the station shown in FIG. 14;

FIG. 16 is a cutting station for cutting the continuous, sealed, laminated web into discrete disposable absorbent products;

DESCRIPTION OF PREFERRED EMBODIMENTS

Figure 1:
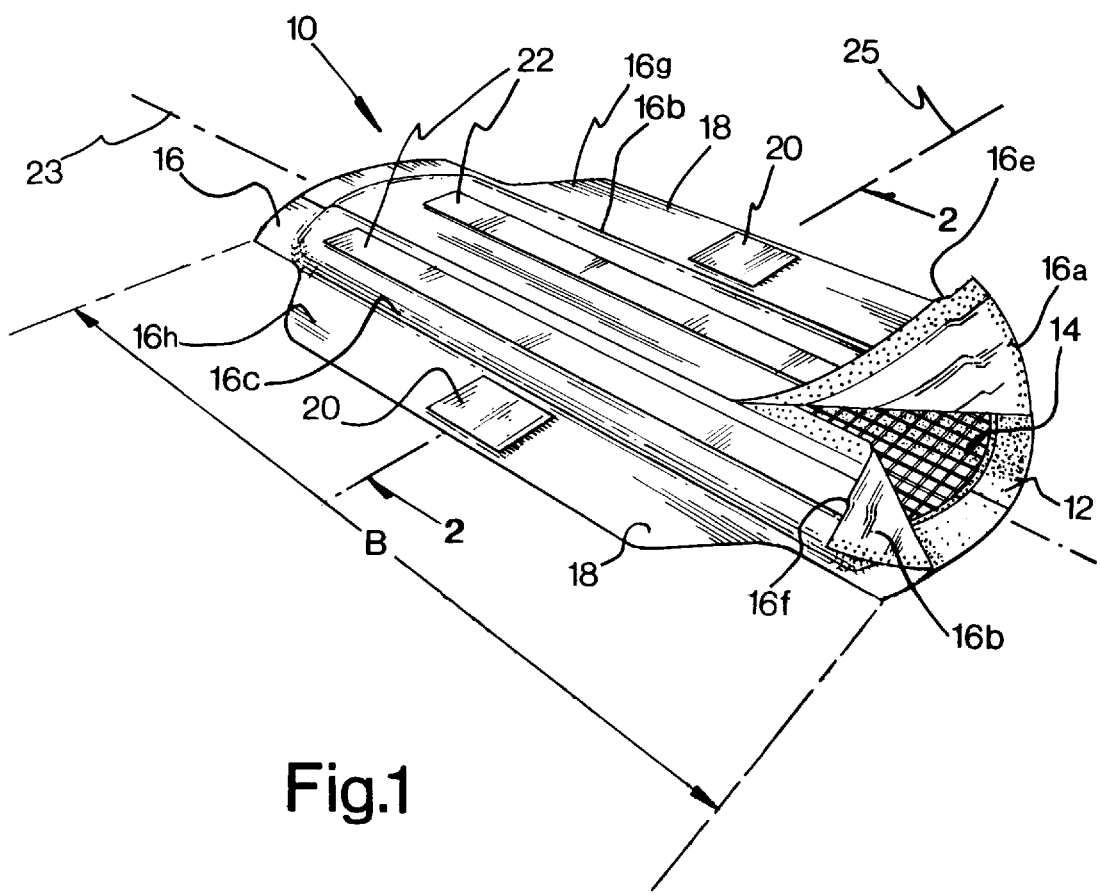
FIG. 1 is a perspective view of a sanitary napkin in accordance with the invention, the fluid-impervious backing layer of the sanitary napkin facing up.

FIGS. 1 to 4 of the annexed drawings illustrate the structure of two disposable absorbent products manufactured by the method according to the invention. FIG. 1 illustrates a sanitary napkin having a laminated construction designated comprehensively by the reference numeral 10. The sanitary napkin 10 comprises a fluid-permeable cover layer 12 made of highly porous non-woven fabric, an absorbent core 14 and a fluid-impervious backing layer 16 made of polyethylene to arrest fluid that may leak through the absorbent core 14.

The sanitary napkin 10 is provided with laterally extending winglets or flaps 18, designed to be folded over the side edges of the wearer's underpants in the crotch portion and to be fastened to the garment facing surface of the underpants. The winglets 18 aid in securing the sanitary napkin 10 in place on the wearer's underpants, and in maintaining the structural integrity of the sanitary napkin 10 by providing a "spring-back" action during body movements of the wearer. The overall effect of the winglets 18 is to fasten and keep the sanitary napkin 10 in an optimal exposed shape to provide the maximum fluid-absorbing surface, whereby reducing the incidence of failures.

To retain the sanitary napkin 10 to the wearer's underpants, adhesive zones 20 and 22 are provided on the backing layer 16. The adhesive zones 20, located over the flaps 18, bond the flaps to the garment facing surface of the wearer's underpants, while the adhesive zones 22 serve to retain the sanitary napkin 10 to the integument facing surface of the underpants.

The contour of the sanitary napkin 10 is symmetrical about two perpendicular axes; a first axis 23 extending longitudinally of the sanitary napkin 10 and a second axis 25 extending transversely of the sanitary napkin 10. Each symmetry axis constitutes an imaginary dividing line about which two opposite and identically shaped edges may be defined on the sanitary napkin 10. For example, the longitudinal symmetry axis 23 defines two symmetrical opposite edges which are the longitudinal edges of the sanitary napkin 10. These edges are not straight but, rather, have a contour displaying a series of angles interconnected by straight lines forming the flaps 18. When considering the transverse symmetry axis 25, the opposite symmetrical edges could be the edges of the front and rear portions of the sanitary napkin 10.

Conventional manufacturing techniques teach that the various layers of the sanitary napkin 10, namely the fluid-permeable cover layer 12, the fluid-impervious backing layer 16 and the absorbent core 14 are made as unitary sheets from the required starting material. Normally, the sheets are dye-cut or otherwise formed from a continuous web. It will be evident to those skilled in the art that such manufacturing techniques will produce an excessive amount of waste material when applied to complex and highly irregular product outlines such as of the sanitary napkin 10.

The present invention provides a solution to this problem and the manufacture of disposable absorbent products such as sanitary napkins, diapers, incontinence pads, adult briefs, wound dressings and the like, having complex shapes, with a limited amount of waste material. The method is an improvement over traditional techniques from the stand point of product cost and environmental safety.

Figure 2:
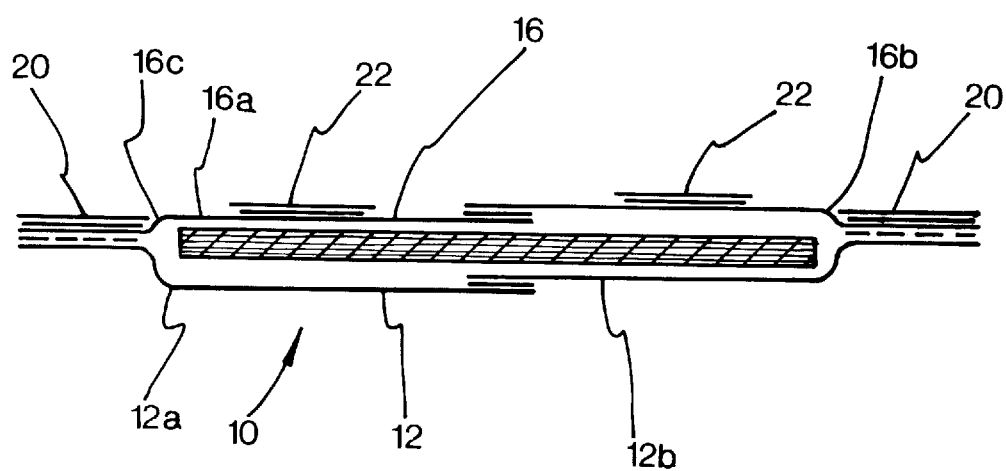
FIG. 2 is a cross-sectional view along lines 2—2 of the sanitary napkin shown in FIG. 1.

As shown in FIGS. 1 and 2, the fluid-impervious backing layer 16 of the sanitary napkin 10 is assembled from two sheets 16a and 16b united in a partially overlapping relationship along the symmetry axis 23 of the sanitary napkin 10. The sheets 16a and 16b are co-planar except at the center of the fluid-impervious backing layer 16 where they overlap and at their marginal portions where they form bends 16c and 16d to merge with the fluid-permeable cover layer 12. For the purpose of this specification, the relationship between the sheets 16a and 16b will be described as "generally co-planar" although in reality the sheets deviate somewhat from a common plane.

The sheets 16a and 16b have identical shapes and together form the symmetrical fluid-impervious backing layer 16. The sheets have straight longitudinal edges 16e and 16f, adjacent to one another, and inflected edges 16g and 16h which form the side edges of the fluid-impervious backing layer 16.

The sheets 16a and 16b may be united directly to one another by adhesive, thermal bonding or any other suitable technique. In a variant, the sheets 16a and 16b may be united by the intermediary of the absorbent core 14. This may be accomplished by individually retaining the sheets 16a and 16b to the absorbent core 14, whereby no direct link exists between the sheets, the absorbent core 14 holding the sheets 16a and 16b together.

As best shown in FIG. 2, the fluid-permeable cover layer 12 is structurally identical to the fluid-impervious backing layer 16. More specifically, it is assembled from two identically shaped sheets 12a and 12b, generally co-planar and being united to one another in a partially overlapping relationship along the longitudinal symmetry axis 23 of the sanitary napkin 10.

Figure 3:
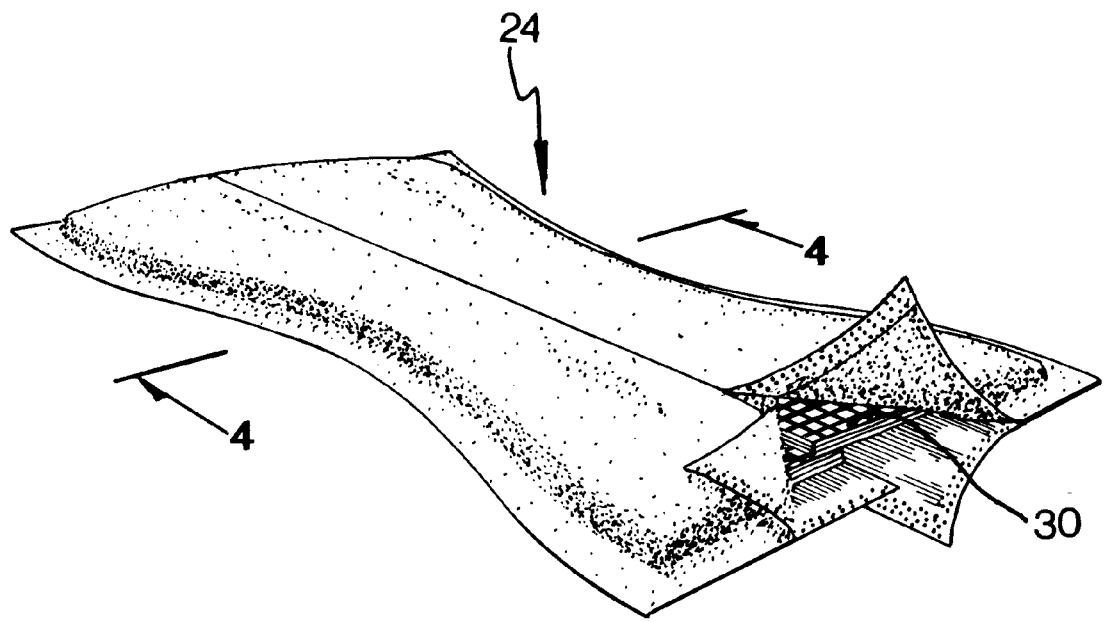
FIG. 3 is a perspective view of a sanitary napkin according to a variant.
Figure 4:
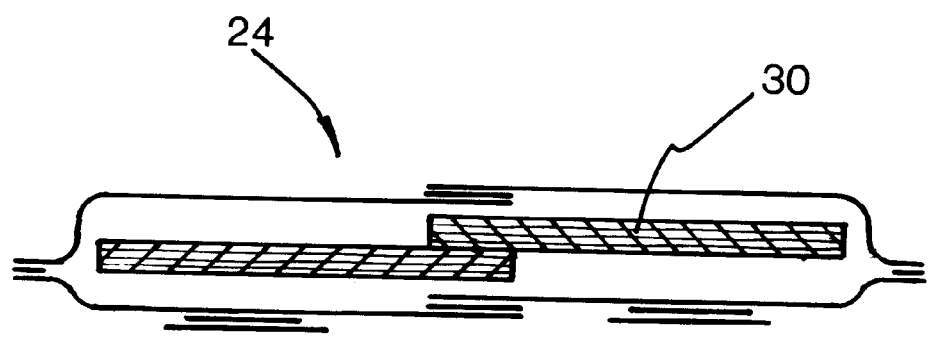
FIG. 4 is a cross-sectional view along lines 4—4 of the sanitary napkin shown in FIG. 3.

FIGS. 3 and 4 illustrate a sanitary napkin 24 constructed according to a variant. This embodiment differs from the sanitary napkin 10 by two significant respects. Firstly, the side edges of the sanitary napkin 24 are anatomically shaped to form recesses, for a better fit between the thighs of the wearer. Secondly, the absorbent core 30 is constructed in a similar manner to the fluid-permeable cover and the fluid-impervious backing layers, i.e. it is made of two planar sections assembled in a partially overlapping relationship.

A compound absorbent core is advantageous for applications where the absorbent layer of the disposable absorbent product is thin and has an irregular shape. Conventional manufacturing processes would produce such irregularly shaped products only with extensive trimming of a unitary sheet of absorbent material, thereby generating a considerable amount of waste. In the embodiment shown in FIGS. 3 and 4, the absorbent core 30 displays profound concavities on the sides, thereby an appreciable reduction in refuse is achieved by assembling the absorbent core 30 from two components. In contrast, the embodiment of FIGS. 1 and 2 uses an absorbent core 14 with straight longitudinal edges which may be cut as a single piece without producing much waste. As a result, the marginal gain in useless by-product reduction may not justify the added complexity of assembling the absorbent core 14 from two components.

In addition, thick absorbent cores may not be suitable for compounding because the overlap at the center of the absorbent core will provide an added thickness which may be undesirable because it creates an elongated bulge reducing the comfort potential of the disposable absorbent product. However, this difficulty may be overcome by adopting a different assembly process which does not involve any overlap of components, such as placing the components of the absorbent core in an abutting relationship to create a joint region flush with the remaining absorbent core.

Figure 5:
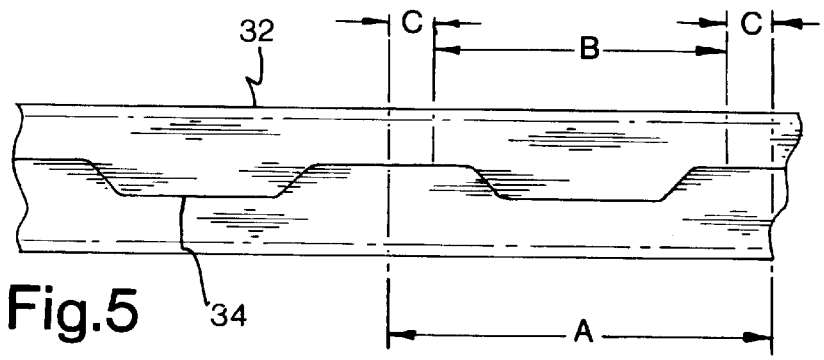
FIGS. 5 to 9 illustrate schematically the steps for assembling the sanitary napkin depicted in FIGS. 1 and 2.

FIGS. 5 to 9 illustrate schematically the various steps of the assembly process of the sanitary napkin 10. A continuous web 32 of fluid-impervious material, such as polyethylene having the desired thickness is cut longitudinally according to a cyclic pattern 34 constituting line segments corresponding to a selected section of the side edge contour of the sanitary napkin 10. In FIG. 5, a single cycle of the cyclic pattern 34 is designated by "A". Cycle "A" comprises a central inflected portion "B" corresponding to a side edge of the sanitary napkin 10 (section "B" is also shown in FIG. 1 for illustrative purposes) and straight end portions "C" at each extremity providing an extra margin, permitting to form the end edges of the sanitary napkin 10 with a projecting shape, such as a convexity as is shown in FIG. 1.

Figure 6:
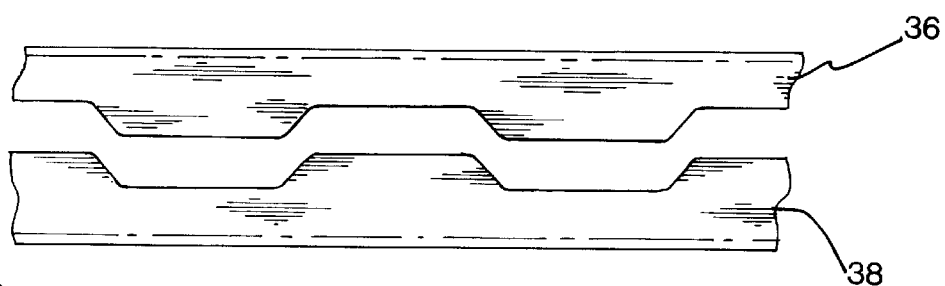

As illustrated in FIG. 6, the cutting operation produces two strips 36 and 38 of fluid-impervious material, each strip having a straight longitudinal edge and an opposite edge which is shaped as the cyclic pattern 34.

Figure 7:
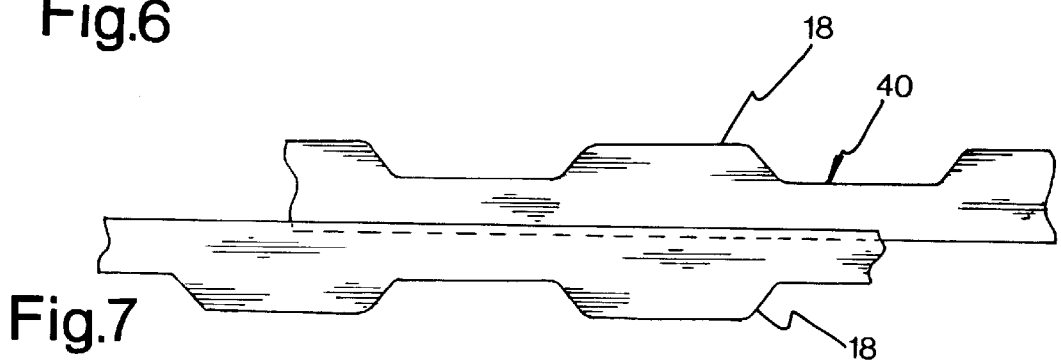
Figure 8:
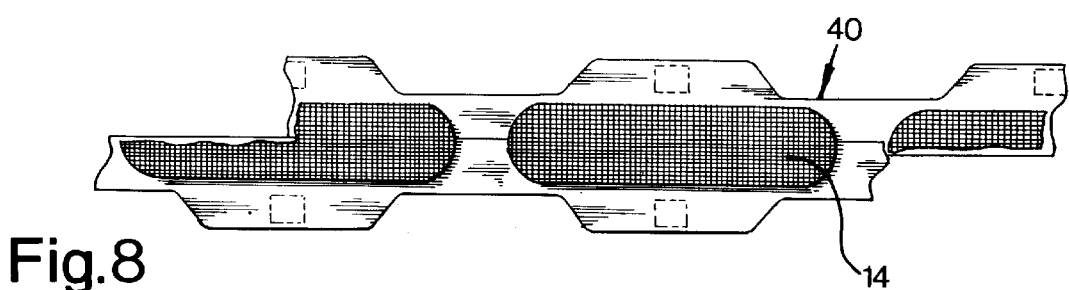

The next step, depicted in FIG. 7, consists of reassembling the strips 36 and 38 side by side with their straight longitudinal edges in adjacency to produce a continuous, compound web 40 having longitudinal edges corresponding to the cyclic pattern 34. Importantly, the strips 36 and 38 are assembled in a predetermined phase relationship, whereby the compound web 40 will repeatedly produce the side edge contour (the flaps 18) of the sanitary napkin 10.

The subsequent step is to serially apply absorbent cores 14 in a spaced apart relationship on the compound web 40. The position of each absorbent core on the compound web 40 is selected according to the positional relationship absorbent core/side edges in the sanitary napkin 10. In the illustrated embodiment, the absorbent cores 14 are centered with respect to the flaps 18.

Figure 9:
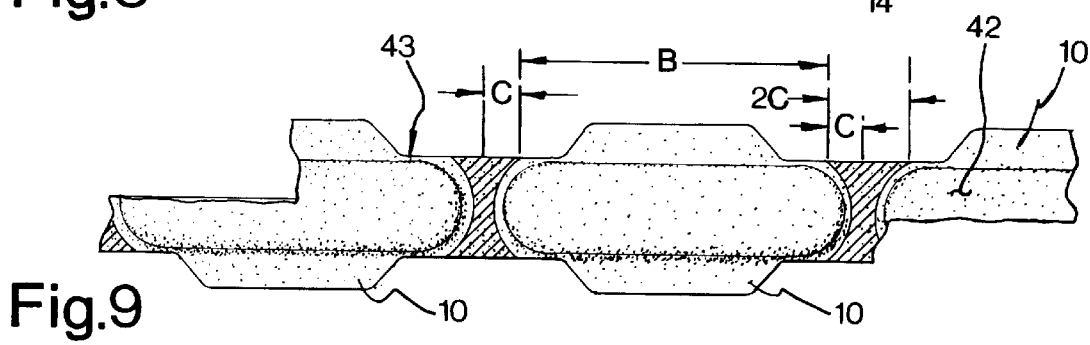

With reference to FIG. 9, a continuous, compound web of fluid-permeable material 42 such as a non-woven fabric, identical in shape to the compound web 40 and constructed in the same manner, is applied thereon in alignment. The compound webs 40 and 42 are retained to one another along the marginal portions of the absorbent cores 14, by adhesive, heat-sealing or any appropriate technique, forming a continuous, laminated, sealed web 43.

The last step of the assembly operation is to cut the continuous, laminated, sealed web 43 transversely between adjacent absorbent cores 14 in order to produce discrete sanitary napkins 10.

With this method, only a limited amount of waste material is produced, identified by the hatched areas in FIG. 9.

FIG. 9 illustrates graphically the importance of providing on extension "C" at each end of the cycle "A". The extension "C" provides an area having a length two times "C" between the side edges of adjacent sanitary napkins 10 on the continuous, laminated, sealed web 43. The area provided by "C" allows the transverse cutting of the web 43 to provide the ends of the sanitary napkins 10 with projecting shapes.

It will be appreciated that no extension "C" is required for applications where the ends of the sanitary napkin are straight and perpendicular to the longitudinal axis of the sanitary napkin as shown in FIG. 2 for example, since a single straight transverse cut of the web 43 simultaneously shapes the adjoining ends of adjacent sanitary napkins.

The various steps of the method for assembling the sanitary napkin 10, briefly described in conjunction with FIGS. 5 to 9, will now be discussed in detail. FIG. 10 illustrates a cutting station 44 where the continuous polyethylene web 32 is cut to form the strips 36 and 38. The cutting station 44 includes a cutter roll 46 provided with a projecting cutting edge 48 acting against an anvil roll 50. The configuration of the cutting edge 48 on the roll 46 determines the cutting pattern.

FIG. 11 illustrates a station 51 for reassembling the strips 36 and 38 into the compound web 40. More specifically, the purpose of the station 51 is firstly, to longitudinally shift one strip with relation to the other in order to obtain the required phase relationship therebetween, and secondly, to unite the strips to one another by their straight edges. The phasing operation is achieved by advancing the strips along paths having different lengths to produce the required longitudinal shift. More specifically, the strip 38 which, at the entry of the station 51 is supported on a conveyor (not shown in the drawing), is raised momentarily above the conveyor surface by an arrangement of rolls 52, 54, 56 and 58. The strip 36 remains continuously in supporting contact with the conveyor. As a result, the runs of the strips 36 and 38 between the rolls 52 and 58 have different lengths, achieving the required phase relationship between the strips.

As best shown in FIG. 12, the strip 38 also moves laterally, while being lifted off the conveyor, for crossing the strip 36 whereby when it is brought back in contact with the conveyor surface, the straight edges of the strips are adjacent to one another. The lateral travel of the strip 38 is controlled so as to bring the strips in a partially overlapping relationship. In the embodiment shown in FIG. 11, an adhesive spray nozzle 60 dispenses adhesive on the margin of the strip 36 which is overlapped by the strip 38. Advantageously, a backing roll 61 is provided under the roll 58 to form a nip, pressing the overlapping portions of the strips 36 and 38 and the adhesive in intimate contact in order to achieve a strong bond.

Figure 13:
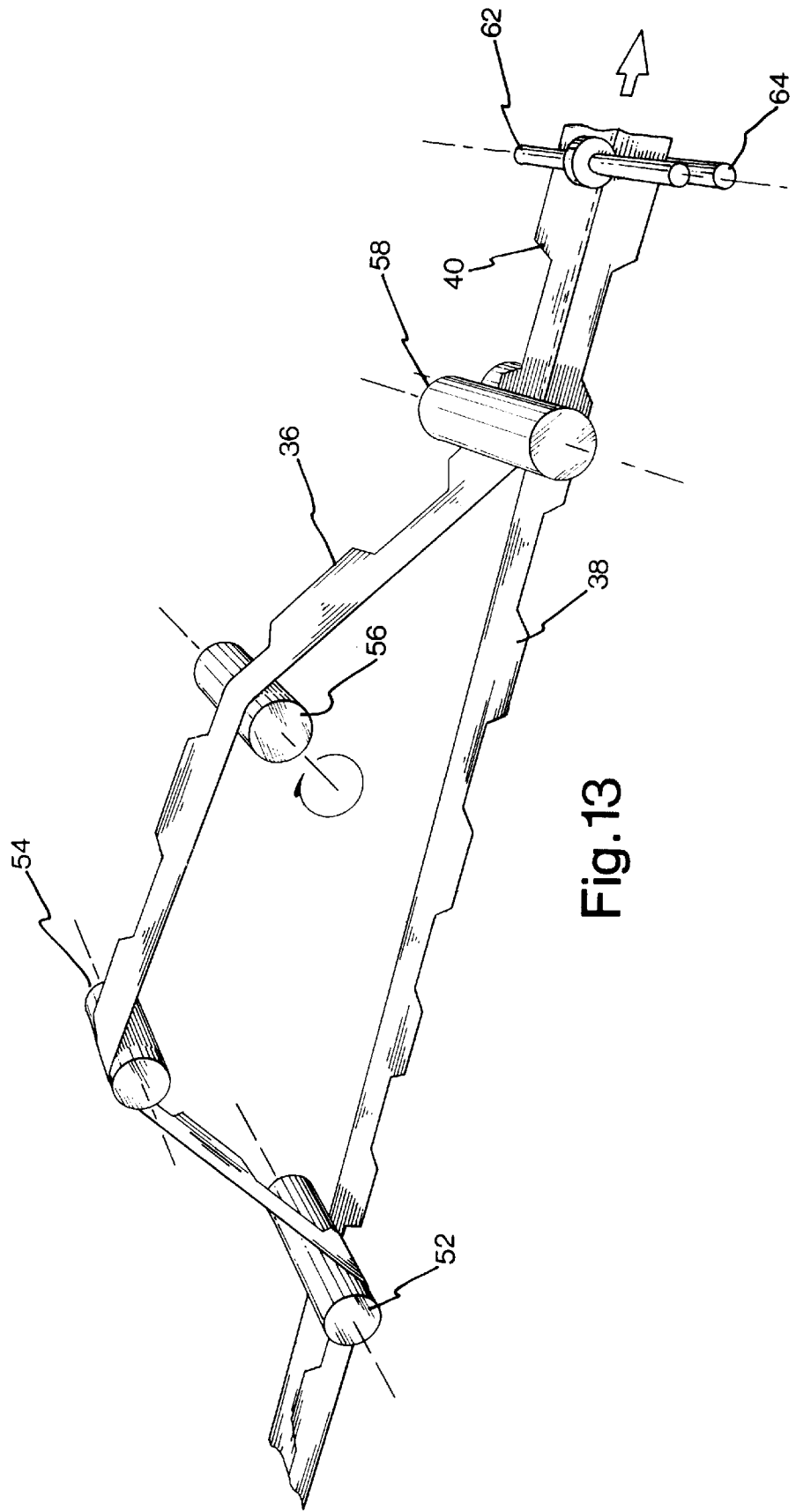
FIG. 13 is a perspective view of a variant of the station shown in FIG. 11.

In a variant depicted in FIG. 13, the strips 36 and 38 are united by a thermal bond created by heated rolls 62 and 64.

FIG. 14 illustrates the final assembly station 70. A conveyor 72 deposits absorbent cores 14 on the compound web 40 in a spaced apart relationship. The operation of the conveyor 72 and the advancement of the compound web 40 are synchronized so that the absorbent cores will be deposited in perfect alignment with the flaps 18 on the compound web 40.

The compound web 42 of fluid-permeable material having a shape identical to the compound web 40, is applied over the absorbent cores 14, in registration with the compound web 40. As mentioned previously, the compound web 42 is manufactured by a method identical to the method for manufacturing the compound web 40 except that a different starting material is used.

A sealing station 78, shown in FIG. 16, located downstream of the assembly station 70, seals the compound webs 40 and 42 to one another around the absorbent cores 14, forming the continuous, laminated, sealed web 43. The sealing operation is performed by a roll 76 acting against a back-up roll 80, and having a recessed portion designed to accept the absorbent cores 14 so that uniform pressure may be applied to secure the remaining portions of the webs 40 and 42 together. The bond between the compound webs 40 and 42 may be achieved by adhesive, applied between the assembly station 70 and the sealing station 80 (not shown in the drawings) or by a thermal bond. The latter embodiment requires a heated pressure roll 78.

FIG. 16 illustrates the last step of the manufacturing operation which is the cutting of the continuous, laminated, sealed web 43 into discrete sanitary napkins 10. This is achieved by a cutting roll 82 which severs the web 43 between adjacent absorbent cores 14 and simultaneously gives a curved shape to the end walls of the sanitary napkins 10.

Figure 17:
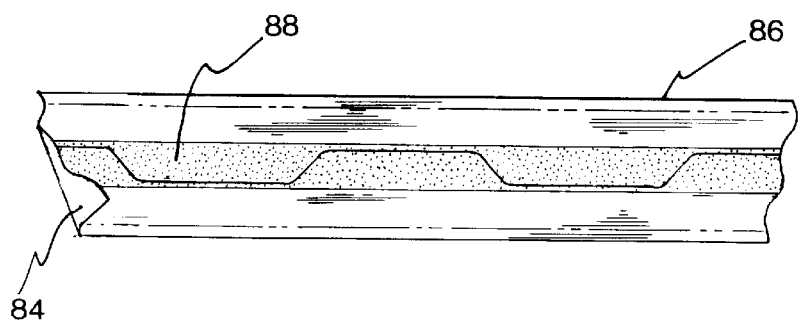
FIGS. 17 to 21 illustrate schematically the steps for assembling a sanitary napkin, according to a variant.
Figure 21:
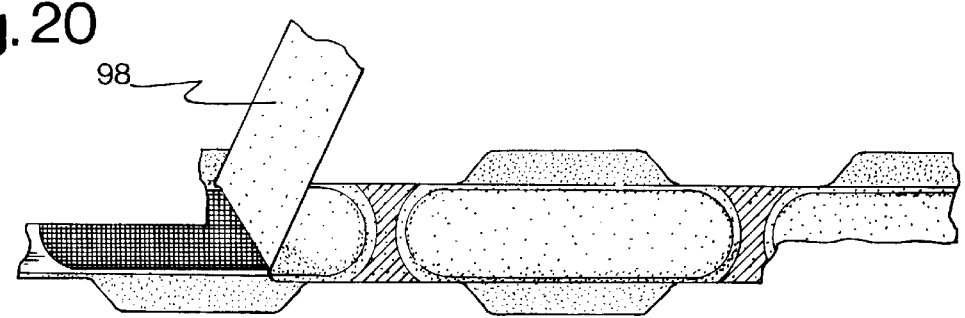

FIGS. 17, to 21 illustrate a method for assembling a sanitary napkin according to a variant.

Referring to FIG. 17, a web of starting material 84 forming the fluid-impervious backing layers of the sanitary napkin is provided, having a laminated construction, comprising a bottom laminae 86 made of fluid-impervious material such as polyethylene and a top laminae 88 of fibrous material such as a non-woven fabric. The top laminae 88 is narrower than the bottom laminae and it is located approximately in the center thereof.

Figure 18:
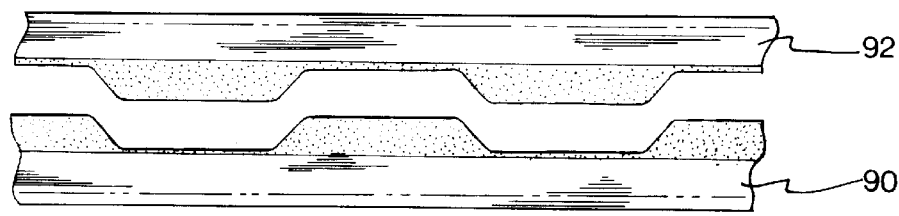

After the cutting operation of the laminated web 84, as shown in FIG. 18, the resulting strips 90 and 92 retain a laminated identity, the fibrous material covering the side edge portions of the strips 90 and 92 whose contour corresponds to the cyclic cutting pattern.

Figure 19:
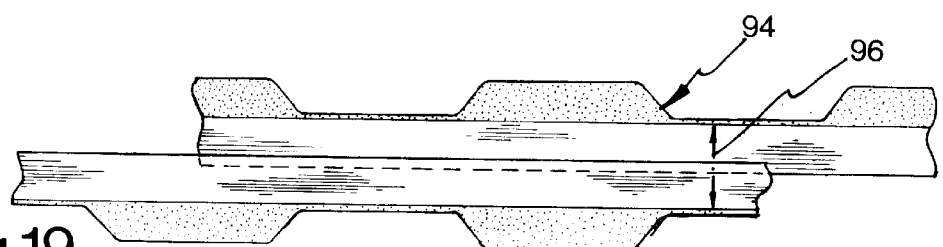
Figure 20:
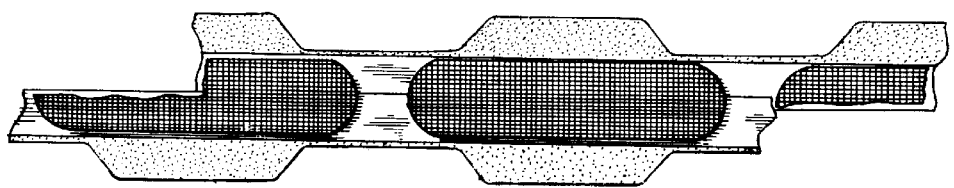

When the strips are reassembled, as shown in FIG. 19, they form a continuous, compound web 94 covered with fibrous material except at a central area 96 where the polyethylene remains exposed for receiving the absorbent cores, as depicted in FIG. 20. With this arrangement, it is no longer required to provide a continuous compound web of fluid-permeable material which mirrors the compound web 94, nor a capability to synchronize the webs feed so that the webs are at all times in alignment. It is sufficient to provide a plain straight sides web 98 of fluid-permeable material, a non-woven fabric for example, to cover the exposed central area 96, since the side edges of the compound web 94 are already furnished with a covering material. This assembly method is highly advantageous because it is simpler than the method described in connection with FIGS. 5 to 9.

FIGS. 22 to 29 illustrate various disposable absorbent product configurations that may be achieved with the method according to the present invention and the corresponding cyclic cutting pattern.

Figure 22:
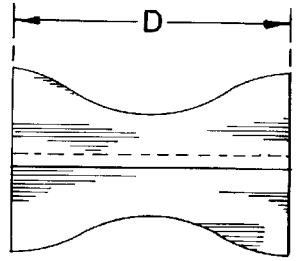
FIGS. 22 to 29 illustrate various shapes of disposable absorbent layers that can be made in accordance with the invention and the corresponding cyclic patterns for cutting the web of starting material.
Figure 23:
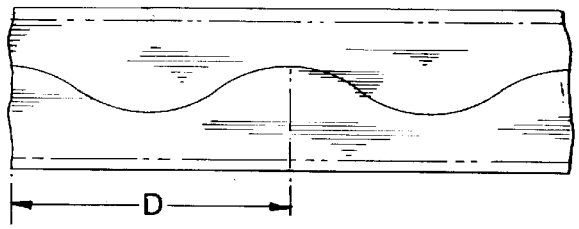

FIG. 22 illustrates in plan view the shape of the sanitary napkin 24. To achieve the concave side-edge pattern, the cutting path, shown in FIG. 23, is sinusoidal. A single cycle of the periodic cutting path is shown by "D".

Figure 24:
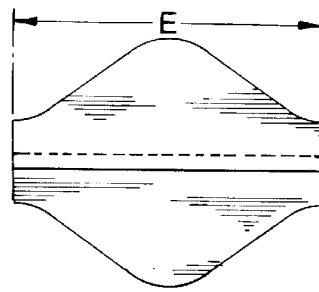
Figure 25:
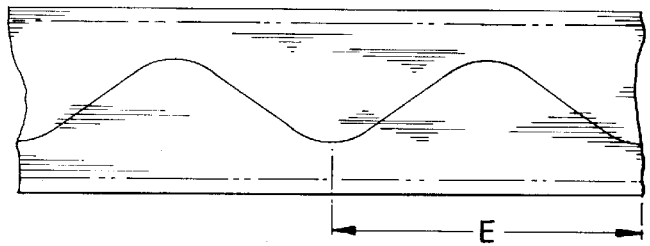

FIG. 24 illustrates a sanitary napkin with convex side edges, providing curved flaps. The cutting path shown in FIG. 25 is again sinusoidal, as in the previous case, except that the transverse cut of the compound web to produce discrete layers is made at a different location. A cycle of the cutting path is shown by "E".

Figure 26:
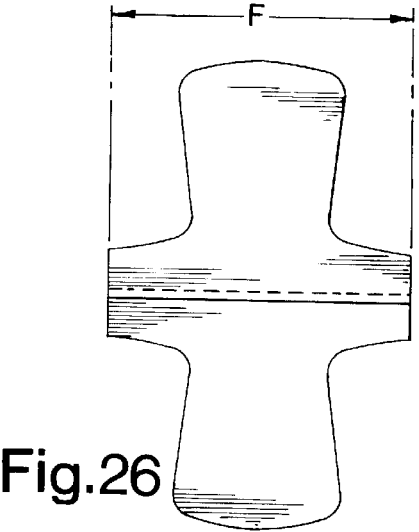
Figure 27:
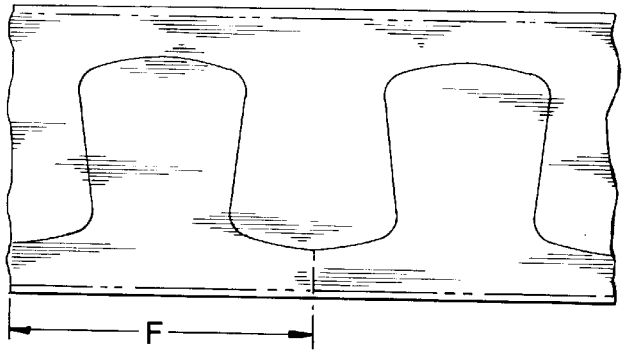

FIG. 26 illustrates a sanitary napkin layer made from two components united to one another along the transverse symmetry axis of the sanitary napkin, not the longitudinal symmetry axis. The corresponding cutting pattern is shown in FIG. 27. A cycle of the cutting path is identified by "F".

Figure 29:
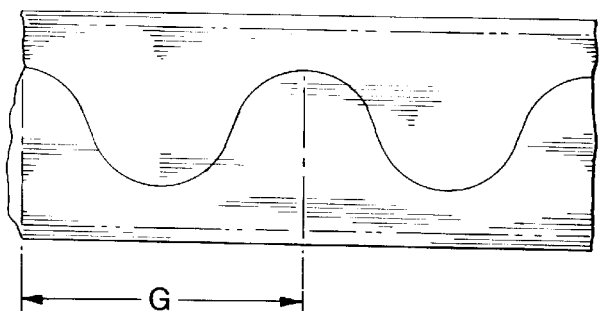
Figure 28:
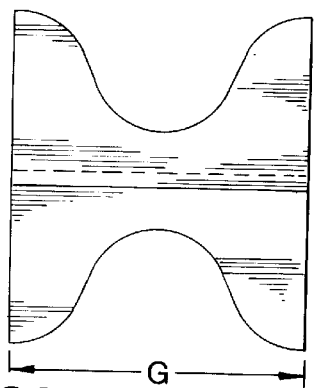

FIG. 28 illustrates a diaper or an adult disposable brief which is similar to the sanitary napkin of FIG. 18 except that it is larger. The method of this invention is particularly advantageous for such application that would require, with conventional manufacturing techniques, side edge trimming producing a considerable amount of waste material. The cutting pattern for this example is shown in FIG. 29. The cycle of the cutting path is identified by "G".

The scope of the present invention is not limited by the description, examples and suggestive uses herein and modifications can be made without departing from the spirit of the invention. Applications of the product and methods of the present invention for sanitary and other health-care uses can be accomplished by any sanitary protection, incontinence, medical and absorbent methods and techniques as are presently or prospectively known to those skilled in the art. Thus it is intended that the present application covers the modifications and variations of this invention provided that they come within the scope of the appended claims and their equivalents.

What is claimed is:

1. A method for manufacturing laminated, disposable absorbent product, each absorbent product comprising a fluid-permeable cover layer and a fluid-impervious backing layer in a parallel and in a spaced apart relationship, and an absorbent core between said layers, one of said layers having two opposite edges with inflected contours, said absorbent core being in a predetermined positional relationship with respect to said opposite edges, said method comprising the steps of:
   providing a continuous web having a laminated structure, including a laminae of fluid-permeable material and a laminae of fluid-impervious material;
   longitudinally cutting said continuous web according to a cyclic pattern comprising a combination of line segments corresponding to a selected section of said opposite edges, thereby dividing said web in two strips, each strip having a patterned longitudinal edge whose outline corresponds to said cyclic pattern;
   reassembling said strips in a parallel and in a selected phase relationship, with the longitudinal edges thereof which are opposite said patterned edges being placed in adjacency to produce a compound web having longitudinal edges formed by said patterned edges which are longitudinally matched to produce repeatedly said selected section, said compound web having laminated side edge portions;
   applying absorbent cores in a spaced apart relationship to said compound web at positions selected in accordance with said predetermined positional relationship;
   applying an additional web to free sides of said absorbent cores, one of said compound and additional webs comprising fluid-pervious material and the other of said compound and additional webs comprising fluid-impervious material;
   uniting said webs to retain said absorbent cores captive therebetween; and
   transversely cutting said compound and additional webs between adjacent absorbent cores to produce discrete disposable absorbent products.

2. A method as defined in claim 1, comprising the step of uniting said strips to one another in a partially over-lapping relationship.

3. A method as defined in claim 2, comprising the step of applying adhesive to at least one of said strips to unite said strips.

4. A method as defined in claim 2, comprising the step of thermally bonding said strips to one another.

5. A method as defined in claim 1, comprising the step of advancing said strips along respective paths having different lengths in order to achieve said selected phase relationship therebetween.

6. A method as defined in claim 5, comprising the step of crossing said strips in order to bring the longitudinal edges thereof which are opposite said patterned edges in adjacency.

7. A method as defined in claim 1, comprising the steps of:
   advancing said strips in a generally parallel relationship in a predetermined direction;
   at a first position stationary with respect to said strips displacing one of said strips with respect to the other strips while continuing to advance said strips in the predetermined direction; and
   at a second position stationary with respect to said strips bringing one of said strips back in a parallel relationship with the other strip, thereby runs of said strips between said first and second positions have different lengths causing a longitudinal shift between said strips.

8. A method as defined in claim 7, comprising the step of displacing one of said strips laterally, between said first and second positions, to cross said strips, thereby downstream of said second position the longitudinal edges of said strips which are opposite said patterned edges are in adjacency.

9. A method as defined in claim 1, wherein said compound web is made of fluid-impervious material.

10. A method as defined in claim 9, comprising the steps of,
    longitudinally cutting a continuous web of fluid-permeable material according to said cyclic pattern, thereby dividing said continuous web of fluid-permeable material in two strips of fluid-permeable material, each strip of fluid-permeable material having a patterned longitudinal edge whose outline corresponds to said cyclic pattern; and
    reassembling said strips of fluid-permeable material in a parallel and in a selected phase relationship, with the longitudinal edges thereof which are opposite the patterned edges of said strips of fluid-permeable material being placed in adjacency, to produce said additional web.

11. A method as defined in claim 10, comprising the step of uniting said strips of fluid-permeable material in a partially overlapping relationship.

12. A method as defined in claim 11, comprising the step of applying adhesive to at least one of said strips of fluid-permeable material.

13. A method as defined in claim 11, comprising the step of thermally bonding said strips of fluid-permeable material to one another.

14. A method as defined in claim 1, wherein said additional web is made of fluid-permeable material.

15. A method as defined in claim 1, wherein said absorbent cores are adhesively retained to said compound web.

16. A method as defined in claim 1, wherein said additional web has a shape identical to the shape of said compound web.

17. A method as defined in claim 1, wherein each of said webs has a longitudinally extending symmetry axis.

18. A method as defined in claim 1, wherein said opposite edges have a symmetry axis which extends generally longitudinally with respect to said laminated, disposable absorbent product.

19. A method as defined in claim 1, wherein said opposite edges have a symmetry axis extending generally transversely to said laminated, disposable absorbent product.

20. A method as defined in claim 1, wherein said laminated, disposable absorbent product is selected from the group consisting of sanitary napkins, diapers, incontinence pads, adult briefs and wound dressings.

21. A method as defined in claim 1, wherein said continuous web has a laminated structure, comprising a laminae of fluid-permeable material and a laminae of fluid-impervious material, providing a compound web with laminated side edge portions.

22. A method as defined in claim 21, wherein one of said laminae is narrower than the other laminae to provide a compound web having a central area with a non-laminated structure.

23. A method as defined in claim 22, wherein said additional web has a generally constant width.

* * * * *